United States Patent [19]
Mathias

[11] Patent Number: 5,434,136
[45] Date of Patent: Jul. 18, 1995

[54] TREATMENT OF MOTILITY DISORDERS WITH A GNRH ANALOG

[76] Inventor: John R. Mathias, 1215 Spring Cress La., Seabrook, Tex. 77586

[21] Appl. No.: 965,675

[22] Filed: Oct. 19, 1992

Related U.S. Application Data

[60] Continuation-in-part of Ser. No. 744,977, Aug. 14, 1991, Pat. No. 5,166,192, which is a division of Ser. No. 626,402, Dec. 14, 1990, Pat. No. 5,056,221.

[51] Int. Cl.⁶ ............... A61K 38/00; C07K 5/00; C07K 7/00; C07K 17/00
[52] U.S. Cl. ............................ 514/15; 530/328
[58] Field of Search ................. 514/15; 530/328

[56] References Cited

U.S. PATENT DOCUMENTS

| | | |
|---|---|---|
| 3,853,837 | 10/1974 | Fujino et al. |
| 3,880,825 | 4/1975 | Sakakibara et al. |
| 3,914,412 | 10/1975 | Gendrich et al. |
| 3,917,825 | 11/1975 | Matsuzawa et al. |
| 4,002,738 | 1/1977 | Johnson et al. |
| 4,005,063 | 1/1977 | Gendrich et al. |
| 4,005,194 | 1/1977 | Johnson . |
| 4,008,209 | 2/1977 | Fujino et al. |
| 4,010,261 | 3/1977 | Johnson et al. |
| 4,018,914 | 4/1977 | Johnson . |
| 4,072,668 | 2/1978 | Amoss et al. |
| 4,229,438 | 10/1980 | Fujino et al. |
| 4,409,208 | 10/1983 | Rivier et al. |
| 4,410,514 | 10/1983 | Vale, Jr. et al. |
| 4,472,382 | 6/1985 | Labrie et al. |
| 4,552,764 | 11/1985 | Goodman et al. |
| 4,565,804 | 1/1986 | Rivier et al. |
| 4,569,927 | 2/1986 | Rivier et al. |
| 4,619,914 | 10/1986 | Vale, Jr. et al. |
| 4,652,550 | 3/1987 | Rivier et al. |
| 4,661,472 | 4/1987 | Rivier et al. |
| 4,690,916 | 11/1987 | Nestor et al. |
| 4,725,577 | 2/1988 | Schally et al. |
| 4,740,500 | 4/1988 | Vale, Jr. et al. |
| 4,920,102 | 4/1990 | Gidda et al. |
| 5,068,221 | 11/1991 | Mathias . |
| 5,166,192 | 11/1992 | Mathias . |

OTHER PUBLICATIONS

Carrabba et al., Biol. Abstrs., 82(2), No. 13939, 1986.
Athreya et al., Clin. Immunol. Immunopath., 66/3 pp. 201–211, 1993.
Fukase et al., Chem. Abstr. vol. 87, 1977, No. 149984c.
Catania et al., Arthritis Rheumatism, vol. 32, No. 9, pp. 1186–1188, 1989.
Mathias et al, *Digestive Diseases and Sciences*, 34:F61–F66, 1989.
Vigersky et al., *American Journal of Medicine*, (1982) 73:482–496.
Mathias et al., *Biological Abstracts*, (1989) vol. 88(5), Ref. No. 53452.
Soldani et al., *J. Endocrinol. Invest.*, (1982) 5:393–396.
Mathias and Finelli, *Functional Disorders of the Gastorintestinal Tract, Contemporary Issues in Gastroenterology*, S. Cohen and R. D. Soloway, eds., New York, Churchill Livingstone, (1987) 6:39–58.
Mitchell and Drossman, *Gastroenterology*, (1987) 92:1283.
Margolis et al., *Pain*, (1984) 20:151–156.
Woodhouse and Bockner, *British Journal of Surgery*, (1979) 66:348–349.
Drossman, *Am. J. of Psychiatry*, (1981) 139:1549.
You et al., *Annals of Internal Medicine*, (1981) 95:449–451.

(List continued on next page.)

*Primary Examiner*—Jill Warden
*Assistant Examiner*—A. M. Davenport
*Attorney, Agent, or Firm*—Pravel, Hewitt, Kimball & Krieger

[57] ABSTRACT

A treatment to alleviate the debilitating symptoms of Motility Disorders, including Autonomic Neuropathies associated with autoimmune disease such as Systemic Lupus Erythematosis (SLE). Treatment of patients with analogs of GnRH significantly reduces or eliminates the symptoms of Motility Disorders, including that associated with SLE.

5 Claims, No Drawings

OTHER PUBLICATIONS

Rees et al., *Gastroenterology*, (1980) 78:360–365.
McCallum et al., *Am. J. of Gastroenterology*, (1985) 88:1008–1016.
Wald et al., *Gastroenterology*, (1981) 8:1497–1500.
Weiss, *Annual Review of Physiology*, (1984) 46:43–52.
Yen, *Fertility and Sterility*, (1983) 38:257–266.
Friedman et al., *Fertility and Sterility*, (1988) 49:404–409.
Meldrum et al., *Fertility and Sterility*, (1988) 50:400–402.
Rajfer et al., *Fertility and Sterility*, (1984) 42:765–771.
Davis et al., *Digestive Diseases and Sciences*, (1988) 33:1505–1511.
Mathias et al., *Digestive Diseases and Sciences*, (1985) 30:119–123.
Jan and Jan, *Journal of Physiology*, (1981) 327:219–246.
Mathias, Chemical Abstracts, CA 114(21):199692c.
Valdes et al., Chemical Abstracts, CA 114(9):75352x.
Howland et al., Chemical Abstracts, CA 93(3):19872c.

TREATMENT OF MOTILITY DISORDERS WITH A GNRH ANALOG

This is a continuation-in-part of U.S. Ser. No. 744,977, filed Aug. 14, 1991, and now U.S. Pat. No. 5,166,192 which is a divisional of Ser. No. 626,402, and now U.S. Pat. No. 5,056,221 which issued Nov. 26, 1991.

SPECIFICATION

1. Field of the Invention

The present invention relates to the treatment of functional motility disorders including diseases of the autonomic nervous system of idiopathic or known causes. Treatment of Functional Bowel Disease or disease of the irritable bowel, as well as the autonomic dysfunction of autoimmune diseases such as Systemic Lupus Erythematosus (SLE) with an analog of GnRH is disclosed.

2. Background of the Invention

Motility Disorders include those diseases characterized by an abnormality of the autonomic nervous system. These include diseases of idiopathic or known causes such as Functional Bowel Diseases and autonomic neuropathies of diabetes, scleroderma, and Parkinson's Disease.

Treatment of the diseases of the autonomic nervous system has been limited to a few drugs approved by the Federal Drug Administration. The most common drug therapy has been with metoclopramide, a dopamine antagonist or with acetylcholine agonists such as bethanechol. Such therapy has had limited success in patients with mild to moderate disease symptoms. New experimental drugs tested for the treatment of patients with disease of the Autonomic Nervous System include the drugs domperidone (dopamine antagonist which does not cross the blood-brain barrier) and cisapride which enhances release of acetylcholine. While these experimental drugs provide limited relief of mild to moderate symptoms, they have not been effective for patients with severe symptoms.

Chronic, unexplained abdominal pain, nausea, vomiting and altered bowel habits are common symptoms of the intractable bowel disorders presently called "Functional Bowel Disease" or "Irritable" Bowel Syndrome. The cause and pathophysiology remain unknown, but evidence suggests that the disease may be related to abnormalities of intestinal smooth muscle or the enteric nervous system, or both, and is a systemic problem (Mathias and Finelli, *Contemporary Issues in Gastroenterology*, S. Cohen and R. D. Soloway (eds) Vol. 639–59, 1987).

A recent survey by Mitchell and Drossman (*Gastroenterology* 92:1283–1284, 1987) found that 47% of patients seen by gastroenterologists had functional complaints; i.e., gastrointestinal symptoms in the absence of objective findings. A similar survey of certified specialists in internal medicine indicated that 13% of their patients had chronic pain without objective findings (Margolis et al., Pain 20:151–156, 1984).

In these functional diseases, women are more commonly affected than men, with the ratio approximately 20:1 (women:men) (Mathias and Finelli, 1987). Often these patients are considered psychoneurotic (Woodhouse and Bockner, *Br. J. Surgery* 66:348–349, 1979; Drossman *Am. J. Psychiatry* 139:1549–1557, 1982) and told they must live with their problems. Psychotherapy, in general, has not added much to improve the general condition of those with moderate-to-severe functional disease.

Recognized syndromes of Functional Bowel Disease include Gastroduodenal Motor Dysfunction, Intestinal Pseudo-obstruction both idiopathic and of known cause, Idiopathic Intestinal Hollow Visceral Myopathy/Neuropathy, Severe Intestinal Constipation and Post-Vagotomy Syndromes such as the Roux-en-Y Syndrome. Previously, these diseases were thought to be disorders without an organic basis, however, recent evidence now suggests these diseases involve alterations of both the muscle of the intestinal wall and the nerves of the myenteric plexus (Mathias and Finelli, *Contemporary Issues in Gastroenterology*, Vol. 6, Cohen and Soloway, eds., New York, Churchill Livingstone, 1987, pages 39–58). Recent evidence has also shown abnormal gastrointestinal motility in many patients (You et. al., *Annals Internal Medicine* 95:449–4.51, 1981; Rees et. al., *Gastroenterology* 78:360–365, 1980; and Mathias and Finelli, 1987). Treatment of such patients has been by medications such as opiates, to enhance gastrointestinal motor activity, or antiemetic effect (McCallum, *American Journal Gastroenterology* 88:1008–1016, 1985). Because of their effects on the upper GI tract, dopamine antagonists such as metoclopramide and domperidone have been tested for therapeutic effects. Results of such therapy have varied, depending upon the antagonist, dosage, treatment regimen, and patient population, but in general such therapy appears to lessen the symptoms of disease.

Motility disorders are common in chronic patients as secondary disorders associated with autoimmune diseases such as Systemic Lupus Erythematosus (SLE).

It would be of great utility to provide a novel treatment of Functional Bowel Disease or Motility Disorders which would alleviate the debilitating symptoms which characterize the disease. It would also be of great utility to provide a novel treatment of motility disorders associated with autoimmune diseases such as SLE.

SUMMARY OF THE INVENTION

The present invention provides a method for treating patients inflicted with Motility Disorders associated with SLE comprising administration of a therapeutically effective dosage of an analog of Gonadotropin-releasing Hormone (GnRH). GnRH analogs are peptides which exhibit GnRH-like activities in standard bioassays (e.g., modulation of gonadotropin release in cultures of pituitary cells) and may be agonists or antagonists of GnRH. The preferred analog of GnRH is a peptide similar to the native compound, however substituted with one or more D-amino acids to prevent degradation of the peptide in vivo. Most preferred is an analog of GnRH of the formula:

pGlu-HIS-Trp-Ser-Tyr-X-Leu-Arg-Pro-NHC$_2$H$_5$

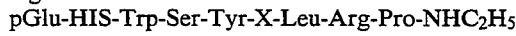

wherein X represents an amino acid in the D-configuration (Seq. Id. No. 2). An especially preferred analog is Lupron wherein X is D-Leu (Seq. Id. No. 3) (TAP Pharmaceuticals, Abbott Labs, North Chicago, Ill. )

Motility Disorders are characterized as those diseases having dysfunction of the Autonomic Nervous System, both idiopathic and of known cause. These include Functional Bowel Diseases and Autonomic Neuropathies of diabetes mellitus, scleroderma, and Parkinson's Disease. Also included is motility dysfunction associated with autoimmune disease such as SLE. The method of this invention is particularly effective in the treatment of patients suffering from Functional Bowel Diseases, including Gastroduodenal Motor Dysfunction, Intestinal Pseudo-obstruction, Idiopathic Intestinal Hollow Visceral Myopathy/Neuropathy, Severe Intestinal Constipation and Post-Vagotomy Syndromes such as Roux-en-Y Syndrome, and in patients presenting severe gastrointestinal dysfunction secondary to autoimmune disease such as SLE.

DETAILED DESCRIPTION OF THE PREFERRED EMBODIMENTS

The cause and pathophysiology of Motility Disorders, including Functional Bowel Disease remain unknown, however evidence suggests that these diseases derive from abnormalities of the autonomic nervous system, for example, the enteric nervous system.

Functional Bowel Disease is more commonly found in women than men at a ratio of approximately 20:1, and the symptoms of abdominal pain, nausea, intermittent vomiting, and changes in stool habits may be exacerbated during the postovulatory phase of the menstrual cycle. During this phase of the menstrual cycle, Luteinizing Hormone (LH), progesterone, and relaxin are secreted. Progesterone is known to alter the function of the gastrointestinal tract in women during the menstrual cycle (Wald et. al., *Gastroenterology* 8:1497–1500, 1981). Relaxins are known to decrease the contractile activity of smooth muscle of the uterus and cause a softening of the symphysis pubis (Weiss, *Annual Review of Physiology* 46:43–52, 1984). The effects of LH and the direct effects of GnRH on smooth muscle or nerve are unknown.

One or more of the above factors, alone or in combination, may act as a provocative substance in altering gastrointestinal function by affecting muscles, nerves, or both. Administration of an analog of GnRH such as the agonist/antagonist leuprolide acetate may inhibit the production of these reproductive hormones and thus provide effective therapeutic relief for idiopathic abdominal pain, nausea, and intermittent vomiting in patients who are debilitated by functional bowel diseases. In addition, GnRH analogs may also exert direct effects upon the autonomic nervous system to provide therapeutic relief of such systems (neurotransmitter).

Naturally occurring GnRH has the following amino acid sequence:

pGlu-His-Trp-Ser-Tyr-Gly-Leu-Arg-Pro-Gly-NH$_2$
(Seq. Id. No. 1)

and is degraded by peptides which cleave the molecule at the Gly$^6$-Leu$^7$ bond and at position 9. Numerous superactive agonistic analogs of GnRH have been synthesized with a D-amino acid substitution at position 6 and often with an ethylamide group in place of the C-terminal glycinamide residue. The increased biologic activity of such peptides has been attributed to their reduced susceptibility to enzymatic degradation, and their high binding affinity to GnRH receptors.

Both GnRH and its agonists possess the potential for inhibition of the pituitary-gonadal axis. Normal GnRH release from the hypothalamus is pulsatile. If the pulsatile pattern of stimulation is substituted by continuous administration of GnRH or its analogs, the gonadotropin-releasing mechanism is inhibited.

Many analogs of GnRH have been synthesized, and their uses in the treatment of reproductive disorders have been disclosed. Known analogs of GnRH are listed in Table 1.

TABLE 1
KNOWN GnRH ANALOGS

| Seq. Id. No. | |
|---|---|
| 4 | pGlu—His—Trp—Ser—A1—Gly—A2—Arg—Pro—NHR (A1 is Tyr or Phe; A2 is Leu, Ile, Val, Met, Phe, nLeu, or nVal) |
| 5 | pGlu—Trp—Ser—Tyr—Gly—Leu—Arg—Pro—Gly—NH$_2$ |
| 6 | pGlu—His—Phe—Ser—Phe—Gly—Leu—Arg—Pro—Gly—NH$_2$ |
| 7 | pGlu—Ala—Trp—Ser—Tyr—Gly—Leu—Arg—Pro—Gly—NH$_2$ |
| 8 | pGlu—His—Trp—Ser—Tyr—X—Leu—Arg—Pro—NH$_2$ (X is an amino acid of D-configuration) |
| 9 | pGlu—His—Trp—Ser—R1—R2—R3—Arg—Pro—NH2R4 (R1 is Tyr or Phe; R2 is a D-amino acid or synthetic amino acid; R3 is Leu, Ile, or nLeu; R4 is His or C$_{1-3}$ alkyl) |
| 10 | pGlu—R1—Trp—Ser—Tyr—R2—Leu—Arg—Pro—Gly—NH$_2$ (R1 is His, Gly, Asp, Cys, or D-amino acid; R2 is D—Ala) |
| 11 | pGlu—His—Trp—Ser—Tyr—X—Leu—Arg—Pro—Gly—NH$_2$ (X is Gly, D-amino acid, or synthetic amino acid) |
| 12 | pGlu—His—Trp—Ser—Tyr—X—Leu—Arg—Pro—Az—Gly—NH$_2$ (X is a D-amino acid; AzG is Gly having OH replaced by N) |

Among the known analogs of GnRH the preferred compounds for use in this invention are peptides with an amino acid of the D-configuration at the 6-position and are forms of leuprolide acetate: D-leu$^6$, Desgly-NH$_2$$^{10}$, prothylamide$^9$ and D-trp$^6$, Desgly-NH$_2$$^{10}$, Prothylamide$^9$; buserelin acetate: D-Ser (Bu$^t$)$^6$, Desgly-NH$_2$$^{10}$, prothylamide$^8$; nafarelin acetate: 3-(2-naphthyl)-D-Ala$^6$; goserelin acetate: D-Ser(Bu$^t$)$^6$, AzGly-NH$_2$$^{10}$; and decapeptyl: D-Trp$^6$.

Additional analogs of GnRH are contemplated as useful in the method of this invention. These include analogs of substituted natural and synthetic amino acids in either the D or L configuration; peptides of greater than or less than 10 amino acids, peptides with varied sugar linkages and additional modifications which do not destroy the agonistic or antagonistic properties of the GnRH analog as measured by bioassay.

GnRH and its analogs are routinely used in the treatment of disorders of the reproductive system. Treatment to stimulate pituitary hormone release in patients with anorexia nervosa, hypogonadotropin anovulation, delayed puberty, cryptorchidism, hypogonadism, and leiomyomata uteri using GnRH analogs has been reported. Treatment to inhibit pituitary hormone release in patients with precocious puberty, endometriosis, hormone-dependant tumors including prostatic mammary carcinomas, polycystic ovarian disease, and treatment for contraceptive purposes have also been reported. To date, known therapeutic uses of analogs of GnRH have been limited to treatment to correct reproductive disorders as disclosed in the patents listed in Table 2.

TABLE 2

| Pat. No. | Inventor | Disorder Treated by GnRH Analogs |
|---|---|---|
| 3,853,837 | Fujino et al. | induction of ovulation |
| 3,880,825 | Sakakibara et al. | controlled release LH |
| 3,914,412 | Gendrich et al. | induction of ovulation |

TABLE 2-continued

| Pat. No. | Inventor | Disorder Treated by GnRH Analogs |
|---|---|---|
| 3,917,825 | Matsuzawa et al. | hormone-dependent tumors |
| 4,002,738 | Johnson et al. | hormone-dependent tumors |
| 4,005,063 | Gendrich, et al. | induction of ovulation |
| 4,005,194 | Johnson | reducing prostatic hyperplasia |
| 4,008,209 | Fujino et al. | induction of ovulation |
| 4,010,261 | Johnson et al. | female contraception |
| 4,018,914 | Johnson | induction of parturition |
| 4,072,668 | Amoss et al. | pituitary release of LH, FSH |
| 4,229,438 | Fujino et al. | immunoregulation |
| 4,472,382 | Labrie, et al. | prostate carcinoma |
| 4,690,916 | Nestor et al. | endometriosis |

The present invention utilizes GnRH analogs in the treatment of a non-reproductive system disorder, namely, the treatment of motility disorders, as exemplified by the Functional Bowel Diseases and Autonomic neuropathies associated with such diseases as Scleroderma, Diabetes Mellitus, and Parkinson's disease.

Without being limited by theory, the therapeutic effect of the GnRH analogs in the treatment of motility disorders is thought to involve the inhibition of the pituitary-gonadal axis. Inhibition of the release of the pituitary gonadotropins Follicle Stimulating Hormone (FSH) and Luteinizing Hormone (LH) is thought to be at least partially responsible for cessation of the debilitating symptoms of the motility disorders. In addition, the inhibition of ovarian secretions including steroids and peptides such as progesterone, relaxin, and inhibin may play a significant role.

Treatment with GnRH analogs is generally by injection, which may be intravenous, subcutaneous, intramuscular, and the like. Treatment may also comprise drug implants with timed release, nasal spray, injection of a long-lasting depo form, or use of other modern advances in drug delivery systems. It is contemplated that oral drug delivery may be possible, but the analog must be one able to maintain the integrity of the peptide through the digestive system. The preferred route of drug delivery is subcutaneous injection. The preferred dosage would vary with the specific activity of the drug to be used, with the severity of the symptoms of the specific patient, but would be sufficient to alleviate the symptoms of the disease.

An additional variable would be the presence/absence of functional reproductive organs, e.g. ovaries. It is expected that the effective subcutaneous dose would be in the range of 0.1 to 5 mg daily, with a preferred range of 0.5 to 1.5 mg daily. It is also contemplated that additional modes of administration of the drug may be used, and that lower or higher doses may then be used, or that treatment may differ from the daily administration illustrated. For example, a lower dose may be administered by a continuous flow-pump, or a higher dose administered in a depo form approximately once per month. The required dose is one which will reduce the particular symptoms of each individual patient.

The following examples are intended to exemplify one mode of use of the present invention, and are not intended to be limiting in scope or specifics.

EXAMPLE 1

Treatment of Five Patients with Leuprolide Acetate

Patients: Four of the five patients tested were women with functional bowel disease: two with gastrointestinal motor dysfunction (GMD), and two with idiopathic intestinal hollow visceral myopathy/neuropathy (IIHVN). The fifth patient had Roux-en-Y Syndrome. All patients had severe, incapacitating symptoms of abdominal pain, nausea, and intermittent vomiting. All had made frequent visits to emergency rooms, had seen many physicians, and undergone multiple tests and surgical procedures, and were unable to maintain their jobs or quality of life. They had been treated with many different drugs, including experimental drugs by protocol. They had difficulty in maintaining body weight, because their symptoms were worsened by eating.

The symptoms of the two patients with GMD were abdominal pain located in the right upper quadrant and epigastrium, daily nausea, and intermittent vomiting exacerbated by eating and by the luteal phase of the menstrual cycle. The two patients with IIHVN had abdominal pain, nausea, and intermittent vomiting, and also had urinary tract involvement consisting of pain and a decrease in urination. The fifth patient had Roux-en-Y syndrome (defined as epigastric-to-right-upper-quadrant pain, nausea, and vomiting increased by eating) after surgical construction of a gastro-jejunal Roux-en-Y anastomosis. The mean duration of these symptoms was eight years (Table 1). All subjects had undergone extensive blood testing, several upper gastrointestinal x-ray series, barium enemas, esophagogastroduodenoscopy, endoscopic retrograde cholangiopancreatography, gastric emptying tests with radiolabeled meal, ultrasound of the abdomen, computerized axial tomography of the abdomen, and many other tests. The results of all tests were normal, except for prolonged gastric emptying in the patient with the Roux-en-Y Syndrome. Because of their intractable clinical problem, these patients were included in the test protocol with leuprolide acetate. Protocol: The symptoms of each patient were first assessed, and their tests evaluated. Each patient kept a daily symptom diary. Leuprolide acetate was obtained by prescription as Lupron (TAP pharmaceuticals, Abbott Labs, North Chicago, Ill.). One multi-use vial of Lupron comprised of 140 mg/2.8 ml Leuprolide Acetate. A daily dose of 0.5 mg (100 $\mu$m) was self-administered by subcutaneous injection, for a period of three months. Each patient was examined at 0, 1 and 3 months of treatment. After the third month, leuprolide was continued as previously, and estrogen (0.625 mg orally) and calcium (1000 mg orally) were also administered. At the end of the sixth month, a two week withdrawal period from leuprolide acetate ensued. During this period a 10 mg oral dose of progesterone was given to pre-menopausal patients, to assess recurrence of symptoms and to induce menses. Post-menopausal women were not treated with progesterone during the two week withdrawal period. This procedure was then continued for an additional six months, with drug withdrawal and progesterone given every three months to induce a menstrual cycle. Serum estradiol, progesterone, FSH, and LH were quantitated by radioimmunoassay prior to the initiation of leuprolide treatment, and at three months post treatment initiation.

Results: Table 3 shows the clinical data on the five women studied. The mean age was 33.0 +/−2.43 years, ranging from 28 to 41 years. The mean duration of symptoms was 8.0 +/−2.02 years prior to the initiation of leuprolide therapy.

TABLE 3

| Patient Number | Age (Years) | Symptom Duration (Years) | Prior Diagnosis | Surgery | Prior Therapy |
|---|---|---|---|---|---|
| 1 | 28* | 6.5 | GMD | None | Ephedrine Lidamidine Domperidone Tylox |
| 2 | 41* | 5.0 | GMD | Tubal Ligation | Lidamidine Domperidone Percodan |
| 3 | 31 | 16.0 | IIHVN | TAHBS/O° 95% Cholestomy | Demerol Tylox |
| 4 | 29 | 7.0 | IIHVN | Laproscopy | Demerol |
| 5 | 36* | 6.0 | Roux-en-Y | Vagotomy Roux-en-Y | Demerol |

°TAHBS/O: Total abdominal hysterectomy with bilateral salpingo-oophorectomy
*Pre-menopausal The results of the leuprolide therapy on the patients' symptoms are shown in Table 4. The results of hormone assays prior to and after treatment with leuprolide for three months is shown in Table 5. When leuprolide treatment was stopped, and a progesterone challenge given to induce menstruation, all subjects experienced recurrent symptoms within three to five days. Each subject had severe symptoms, some required hospitalization.

TABLE 4

Symptoms Before and After Leuprolide Acetate

| Patient | Before | After |
|---|---|---|
| 1. | Pain. RUQ*, epigastrium, BLQ° | Abolished |
|  | Nausea, daily | Decreased considerably |
|  | Intermittent vomiting | Abolished |
|  | Worsened by ovulation | — |
|  | Constipation | Daily formed stools |
| 2. | Epigastric to RUQ pain | Abolished |
|  | Nausea, daily | Abolished |
|  | Worsened by ovulation | — |
|  | Constipation, intermittent | Daily formed stools |
| 3. | Epigastric to RUQ pain | Decreased considerably |
|  | Bilatekal lower quadrant pain | Abolished |
|  | Nausea, daily | Abolished |
|  | Obstipation | Daily formed stools |
|  | Pain on urination | Abolished |
| 4. | Deep boring pain in lower abdomen and rectum | Abolished |
|  | Constipation and urinary difficulty after ovulation | Daily formed stools, normal urination (4–6 ×/day) |
| 5. | Epigastric to RUQ pain | Abolished |
|  | Worsened by eating | Abolished |
|  | Nausea, daily | Abolished |
|  | Intermittent vomiting | Abolished |
|  | Diarrhea | Daily formed stools |

*RUQ: right upper quadrant
°BLQ: bilateral lower quadrant

TABLE 5

Gonadotropin Levels Before Leuprolide Therapy and After Three Months

| Patient No. | Gonadotropin | Baseline | After 3 Months |
|---|---|---|---|
| 1. | Estradiol | 44.0 pg/ml | 13.0 pg/ml |
|  | Progesterone | 3.0 n/ml | <0.25 n/ml* |
|  | LH | 19.0 mIU/mL | 6.0 mIU/ml° |
|  | FSH | 12.1 mIU/ml | 9.0 MIU/ml |
| 2. | Estradiol | 44.0 pg/ml | 39.0 pg/ml |
|  | Progesterone | 1.0 n/ml | <0.25 n/ml* |
|  | LH | 16.0 mIU/ml | 7.0 mIU/ml° |
|  | FSH | 13.0 mIU/ml | 11.0 MIU/ml |
| 3. | Estradiol | 28.0 pg/ml | 3.4 pg/ml |
|  | Progesterone | <0.25 n/ml | <0.25 n/ml |
|  | LH | 18.4 mIU/ml | 11.2 mIU/ml° |
|  | FSH | 32.0 mIU/ml | 11.2 mIU/ml |
| 4. | Estradiol | 20.0 pg/ml | 5.5 pg/ml |
|  | Progesterone | 3.0 n/ml | <0.25 n/ml* |
|  | LH | 18.3 mIU/ml | 5.0 MIU/ml° |
|  | FSH | 13.1 mIU/ml | 7.9 mIU/ml |

*P < 0.006
°P < 0.0004 (all values expressed as the mean + SEM of all four subjects), compared with the baseline.
**Total abdominal hysterectomy and bilateral salpingo-oophorectomy Patients with GMD became symptom-free after treatment with leuprolide. Patient 3 (with IIHVN) responded dramatically despite having had a total abdominal hysterectomy and bilateral salpingo-oophorectomy. After leuprolide therapy, nausea and vomiting subsided, and she developed normal bowel and bladder function. She does continue to experience mild and intermittent abdominal pain; however, the quality of her life has been restored, and she has returned to work. Patient number 4 with IIHVN is now symptom-free. Patient number 5, with Roux-en-Y also responded dramatically to leuprolide, therapy, is symptom-free and gained 35 pounds, increasing from 96 to 131 pounds.

Treatment with leuprolide resulted in a significant decrease in the levels of serum progesterone and LH. Estradiol and FSH levels also decreased.

These results indicate that treatment with leuprolide acetate, a potent GnRH analog, successfully reduces or abolishes the debilitating symptoms of patients with Motility Disorders.

EXAMPLE 2

Treatment of Additional Patients Having Functional Bowel Disorders

The procedure of example 1 was followed with additional patients. These patients exhibited a range of functional bowel disorders as shown in Table 6. The majority of patients exhibited full recovery from symptoms of their disease in response to leuprolide treatment (Responded). Four patients of the twenty-six treated to date failed to respond to the treatment (Failure). One of those who failed to respond was withdrawn from treatment due to side effects of bone pain (Side effects), and one expired as a result of bacterial endocarditis (Failure expired). One patient listed as a failure elected to withdraw from the program after four weeks of treatment. One patient after recovering from the symptoms of her autonomic neuropathy expired from a massive myocardial infarction (Responded—expired).

TABLE 6

| Diagnosis | Patient No. | Response |
|---|---|---|
| Idiopathic Intestinal Hollow | 13 | Responded |
| Visceral Myopathy/Neuropathy | 18 | Responded |
|  | 26 | Just begun treatment |
| Gastrointestinal Motor Dysfunction | 17 | Responded |
|  | 19 | Responded |
|  | 20 | Responded |
|  | 21 | Responded |
|  | 22 | Responded |
|  | 24 | Just begun treatment |
| Pelvic Floor Dysfunction | 7 | Responded |

TABLE 6-continued

| Diagnosis | Patient No. | Response |
| --- | --- | --- |
| | 14 | Failure |
| Chronic Intestinal Pseudo Obstruction | 8 | Responded |
| | 11 | Failure - side effects |
| | 15 | Responded |
| Roux-en-Y-Syndrome | 9 | Responded |
| | 10 | Failure - withdrew |
| | 12 | Failure - expired |
| | 16 | Responded |
| | 23 | Responded |
| | 25 | Just begun treatment |

*Pre-menopausal

The symptoms of Idiopathic Intestinal Hollow Visceral Myopathy/Neuropathy include recurrent postprandial (worsened by eating) abdominal pain, distension of the stomach and small intestine, and intermittent vomiting. This disease also affects other hollow viscera, such as the alimentary tract, the ureters, the bladder, and the urethra. Fibrosis of the lens of the eye and the presence of hepatic portal fibrosis may also be associated. Frequently, lower quadrant pain is associated, and may involve fallopian tube dysfunction.

The symptoms of Gastroduodenal Motor Dysfunction are unexplained chronic nausea, abdominal pain (usually right upper quadrant or epigastric and worsened by eating, stress, and post-ovulation) and intermittent episodic vomiting.

Patients Having Chronic Intestinal

Pseudoobstruction complain of frequent and intermittent episodes of abdominal distention, nausea and may have episodic vomiting. X-rays of the abdomen may disclose air/fluid levels suggestive of mechanical obstruction. Chronic Intestinal Pseudoobstruction may include dilation of the small bowel, the dilation of the colon, and also severe gastric atony. Normal neural responses to swallowing and intestinal distention may be impaired.

The symptoms of the patients having pelvic floor dysfunction include deep boring pain in the rectum and lower abdomen with altered bowel and urinary habits. This disorder is characterized by dysfunction of the muscles of the pelvic diaphragm. The symptoms of the patients having Post Vagotomy Roux-en-Y Syndrome (as defined in Mathias, *Gastroenterology* 88:101–107, 1985) include chronic nausea, vomiting, and postprandial abdominal pain.

These patients were treated with Leuprolide acetate following the protocol established in Example 1.

Patient Number 13 is a 36 year old white woman first seen in 1976 for recurrent abdominal pain. Between 1976 and 1978 she underwent an exploratory laparotomy, cholecystectomy (no stones), and a sphincteroplasty of the sphincter of Oddi, however her symptoms worsened. In 1981, she underwent duodenal jejunal manometry of her small intestine which revealed a several motor disorder consistent with chronic intestinal pseudoobstruction. She had been a participant in several experimental protocols with minimal success. Her symptoms progressed to include difficulty in urination. Leuprolide acetate therapy according to the protocol of example 1 was initiated in May, 1988. Her symptoms improved dramatically, she no longer requires parental alimentation for weight control, and urination has improved.

Patient Number 18 is a 40 year old white woman who had long standing problems with nausea, abdominal pain, obstipation, and infrequent urination. When referred for evaluation, her disease was debilitating and she was unable to work. Leuprolide acetate therapy according to the protocol of example 1 was begun in November, 1988. Currently, all of her symptoms have improved except for her obstipation.

Patient Number 17 is a 38 year old white woman referred for evaluation of nausea and chronic abdominal pain. She also suffers from long standing chronic obstructive lung disease requiring multiple therapies for her breathing. An upper gastrointestinal X-ray series, upper endoscopy and ultra sound of the abdomen were normal. Leuprolide acetate therapy according to the protocol of example 1 was begun in July, 1988. Her symptoms of nausea and chronic abdominal pain have abated. In addition, a smaller dose of Theophylline is now required for her lung disease, with dramatic improvement in pulmonary function tests seen.

Patient Number 19 is a 43 year old white woman referred for nausea and right upper quadrant pain. Upper gastrointestinal endoscopy, upper gastrointestinal X-ray series, and computerized axial tomography of the abdomen all displayed normal results. Endoscopic retrograde cholangiopancreatography disclosed a possible defect of the cystic duct of the gallbladder. Cholecystectomy was performed; however, the gallbladder bed was normal and no stones were found. Postoperatively, the patient's symptoms persisted. Leuprolide acetate therapy according to the protocol of example 1 was begun in August, 1988. After 6 weeks of leuprolide acetate therapy, all symptoms had disappeared. After six months of treatment, the patient was symptom free. The drug was discontinued in March 1989 with no recurrent disease.

Patient Number 20 is a 65 year old white women referred for nausea, abdominal pain and constipation of many years duration. After extensive evaluation by many previous physicians this patient was told her problem was "in her head and she would just have to live with it". Leuprolide acetate treatment according to the protocol of example 1 was begun in October, 1988. The patient is now symptom-free.

Patient Number 22 is a 23 year old white woman referred for a 5 month history of nausea, vomiting, abdominal pain, and the inability to swallow even her own saliva. She had been extensively evaluated, however no known diagnosis was found. In November, 1988 evaluations showed a positive Epstein Barr titer of 1:1280 indicating ongoing chronic mononucleosis and associated gastroduodenal motor dysfunction. Leuprolide acetate therapy according to the protocol of example 1 was begun in December, 1988. A dramatic response was seen after three weeks of therapy. This patient is now able to swallow and eat.

Patient Number 7 is a 67 year old white woman seen in April, 1988 complaining of severe deep boring rectal pain. She had previously been evaluated by many physicians and was treated with antidepressants without relief. Conventional testing including upper gastrointestinal X-ray series, barium enema, colonoscopy, and Computerized Axial Tomography of the abdomen all gave normal results. Leuprolide acetate therapy according to the protocol of example 1 was begun in June, 1988.

Within 8 weeks of therapy, this patient was symptom free.

Patient Number 8 is a 36 year old white woman first seen at the VA Hospital in Gainesville, Fla., 1977. She had been in the army and was given a medical discharge for chronic abdominal pain. Extensive evaluation including laparotomy and cholecystectomy indicated no cause of disease. In 1981, duodenal jejunal manometry of her stomach and small intestine revealed severe motor disease consistent with intestinal pseudoobstruction. Since that time she has participated in several experimental protocols without relief. Since 1985, this patient was admitted to the hospital at least one week per month for nasogastric suction, hydration, decompressive colonoscopy, and medical therapy. Treatment with leuprolide acetate according to the protocol of Example 1 was begun in September, 1988. Since beginning leuprolide acetate treatment, this patient does not chronically experience severe symptoms, and has had no hospital admissions since this drug therapy was begun.

Patient Number 15 is a 38 year old white woman who experienced abdominal distention, fever, and was unable to maintain oral intake. She was extensively evaluated at several institutions with no diagnosis reached. When evaluated in 1988, she required parental hyperalimentation for weight control. She had undergone exploratory laparotomy which revealed only acute/chronic inflammation. Leuprolide acetate therapy according to the protocol of example 1 was begun in March 1988. Her symptoms have steadily improved, and she now requires no parental supplementation. She has returned to work.

Patient Number 16 is a 60 year old white woman with long standing nausea, vomiting, and abdominal pain following a gastro-jejunostomy Roux-en-Y anastomosis for alkaline reflux gastritis secondary to a truncal vagotomy and Billroth II for intractable idiopathic peptic ulcer disease. Her weight was 96 pounds. Leuprolide acetate therapy according to the protocol of example 1 was begun in August, 1988. Her symptoms have been relieved, and she is now able to eat and maintain her ideal weight of 115–118 pounds.

Patient Number 23 is a 39 year old white woman who was evaluated in 1984 for chronic nausea, vomiting, and abdominal pain following a gastro-jejunostomy Roux-en-Y anastomosis for alkaline reflux gastritis secondary to a truncal vagotomy and Billroth II for intractable idiopathic peptic ulcer disease. The use of opiates to control her pain caused the loss of her job as a registered nurse. Leuprolide acetate therapy according to the protocol of example 1 was begun in November, 1988. After Lupron therapy, she became symptom free, and did not require opiates for pain.

EXAMPLE 3

Treatment of Patients Having Previous Ovariectomy

Two patients discussed in Example 1 were women who had undergone surgery for removal of their ovaries. The first patient, Number 3, had undergone this surgery approximately two years prior to beginning Leuprolide acetate treatment. The second patient, Number 4, underwent ovariectomy 18 months after beginning treatment with Leuprolide Acetate.

In both cases, the effective dose of leuprolide acetate was higher than the effective dose required by patients who had not had ovaries removed.

Patient Number 3 was given a daily dose of Leuprolide acetate initially at 0.5 mg. This was increased to 2.0 mg in order to overcome her symptoms.

Patient Number 4 was symptom free with the daily dose of 0.5 mg of leuprolide acetate prior to the removal of her ovaries. Post-ovariectomy however, this dose was not sufficient. An effective daily dose of 2.0 mg was found to relieve her symptoms.

EXAMPLE 4

Leuprolide Acetate Effects on Migrating Motor Complexes in Rats

Eleven female Wistar rats weighing between 175 and 250 g were each implanted with four bipolar Ag/AgCL electrodes (the preparation of which is described in: Mathias, *Am. J. Physiology*, 249:G416–G421, 1981). The electrodes were sewn 5 cm from the Ligament of Trietz and 5 cm apart, onto the jejunal serosa. The number of migrating myoelectric complexes was recorded using a R-612 Dynograph (Sensor-Medics, Anaheim, Calif.). Rats were fasted for 36 hours prior to recording and feeding (no food, liberal water), and were housed in special cages to remove feces. After 36 hours of fasting, Migrating Motor Complexes (MMC) were recorded at a sensitivity of 0.2 mV/cm, 2.5 mm/sec paper speed, and a Time Constant of 1 for a duration of 2 to 4 hours. Immediately following the fasted recording session, the rats were fed 2 biscuits of Purina rat chow with simultaneous recording during feeding and continued for 4 hours.

This procedure was followed for 2 to 4 recording sessions prior to the treatment with leuprolide acetate (Controls).

Leuprolide acetate was then administered daily, in the morning, subcutaneously in the hind limb at a dose ranging from 2 to 40 ug/100 g body weight. After a period of at least 24 hours post treatment with leuprolide, the fasting/fed recording sessions were begun as described for the controls to obtain recordings through 2 to 4 sessions. The results are shown in Table 8.

TABLE 8

| | Migrating Motor Complexes (MMC/hour) | | | |
|---|---|---|---|---|
| | CONTROLS | | TREATMENT | |
| Dose | Fasted | Fed | L-Fasted | L-Fed |
| 2 μg | 4.69 ± 0.24 | 2.60 ± 0.27+ | 4.60 ± 0.12 | 4.83 ± 0.65* |
| 20 μg | 4.43 ± 0.25 | 1.40 ± 0.48f | 5.41 ± 0.17 | 4.11 ± 0.22* |
| 40 μg | 4.75 ± 0.48 | 2.33 ± 0.33¶ | 4.48 ± 0.12 | 3.45 ± 0.25* |

*Represents inhibition of the fed-state; all values expressed as the mean ± SEM
+$P < 0.001$, Fed versus Lupron-Fed
f$P < 0.0001$, Fed versus Lupron-Fed
¶ $P < 0.017$, Fed versus Lupron-Fed
L-Fasted and L-Fed denotes Lupron treated animals These results show that the fed state was replaced by cyclin MMCs. Similar to control values in fasted rats with as little as 2 μg/100 g body weight of leuprolide acetate.

EXAMPLE 5

Leuprolide Acetate in Ovariectomized Female Rats

Female Wistar rats were ovariectomized and permitted to recover ten days. Bipolar Ag/AgCl electrodes were then implanted as described for example 4. Control MMC readings in the fasted and fed states were recorded prior to treatment with leuprolide acetate (Controls) as described in Example 4.

Treatment with leuprolide acetate followed using doses in the range of 2 to 250 μg/100 g body weight. Fasted and fed recordings were obtained as described for Example 4. The results of these studies are shown in Table 9.

TABLE 9

Migrating Motor Complexes in Ovariectomized Rats (MMC/hour)

| Dose | OVX-CONTROLS | | OVX-TREATMENT | |
|---|---|---|---|---|
| | Fasted | Fed | L-Fasted | L-Fed |
| 2 μg | 3.86 + 0.14 | 0 | 4.40 + 0.16 | 0 |
| 20 μg | 5.17 + 0.31 | 0 | 5.40 + 0.15 | 0 |
| 40 μg | 4.50 + 0.22 | 0.88 + 0.58 | 5.23 + 0.41 | 0 |
| 100 μg | 4.00 + 0.17 | 0$^t$ | 5.00 + 0.41 | 4.50 + 0.34* |
| 250 μg | 4.50 + 0.22 | 0.88 + 0.58$^f$ | 4.50 + 0.29 | 5.00 + 0.58* |

All values expressed as the mean + SEM;
*denotes inhibition of the fed-state;
$^t$ $p < 0.0001$ Fed versus L-Fed;
$^f$ $p < 0.0001$ Fed versus L-Fed;
L-Fasted and L-Fed denotes Lupron treated animals.

These results show that higher doses of leuprolide acetate (100 ug/100 g body weight) are required to overcome the reduction of MMC/hour in fed female rats.

EXAMPLE 6

Treatment of End Stage Scleroderma

Scleroderma is defined as a chronic disease of unknown cause, characterized by diffuse fibrosis, degenerative changes, and vascular abnormalities in the skin, articular structures, and internal organs, especially the esophagus, gastrointestinal tract, thyroid, lung, heart, and kidney.

Patient number 6 was in end-stage scleroderma. She had been bed-ridden for approximately eight months, unable to retain food after eating, and was being maintained on total parental hyperalimentation (TPN) to keep up body weight and fluid and electrolyte balance for five months.

This patient was treated with 0.5 mg Leuprolide acetate daily, by subcutaneous injection according to the protocol of example 1. After five weeks of therapy, she was able to move about actively, and did not require the TPN feeding. She was discharged from the hospital, was eating without difficulty, and had gained weight.

After four months of therapy, and recovery from the gastrointestinal problems associated with her disease, this patient suffered a severe myocardial infarction and expired. Her death was attributed to the duration and complications associated with her disease and did not implicate the use of the medication given.

EXAMPLE 7

Treatment of irritable bowel disease with GnRH analogs Nafarelin and Danazol B. W., a 28 year old male patient suffering from irritable bowel syndrome presented symptoms of nausea, vomiting, abdominal pain, and altered bowel habits. This patient was treated with lupron, 2.0 mg/day by subcutaneous injection, for a period of six months. Treatment with lupron effectively reduced the symptoms of his irritable bowel disease and effectively reduced his blood levels of FSH and LH, however, side effects from the lupron therapy included impotency and bone pain. In order to avoid these side effects, lupron therapy was discontinued, and treatment with another GnRH analog, Nafarelin, was begun at 2.0 mg/day by subcutaneous injection for a period of three months. Nafarelin is a GnRH analog available from SYNTEX, which differs from the natural GnRH peptide in a D-Nal (2)$^6$ substitution. Treatment with Nafarelin effectively reduced the symptoms of his irritable bowel disease, and effectively reduced his blood levels of FSH and LH, but induced side effects of severe headache, flu-like symptoms, and impotency. Nafarelin therapy was discontinued, and treatment with Danazol, a 17-ethyltestosterone derivative known to antagonize GnRH receptors at the level of the pituitary, was begun, at 200 mg four times daily, P.O., for a period of three months. Treatment with Danazol had only minimal therapeutic effect in this patient. Danazol therapy was discontinued, and the patient resumed Lupron therapy, administered as a depot of 7.5 mg, I.M., monthly, with additional monthly injections of 100 mg of testosterone depot, I.M., to control impotency. After six months of this treatment regimen, his irritable bowel symptoms were controlled without side effects, and his impotency had subsided.

EXAMPLE 8

Treatment of Five Patients Suffering from GI Disorders Secondary to Systemic Lupus Erythematosus Patient number 1 (S.H.) was a 44 year old female who presented with severe and life threatening symptoms that were diagnosed as SLE in 1986. Her diagnosis of SLE was thought to be associated with silicon leakage from breast implants. She required systemic Imuran and prednisone to control her symptoms. After induction of remission, she required significant daily doses of Imuran and prednisone by mouth to sustain the remission. Over the ensuing period of three to four years, she slowly develop chronic nausea, intermittent vomiting, and severe abdominal pain. She was extensively evaluated with X-rays, endoscopic procedures, imaging procedures (CT and MRI), however, all these tests remained normal.

She was evaluated with duodenal jejunal manometry and demonstrated relatively little activity of the stomach and small intestine. A hydrogen breath test, which measures oral to cecal transit time, was administered and demonstrated markedly prolonged transit time. She was diagnosed with chronic intestinal pseudo-obstruction secondary to SLE.

Daily treatment with 2.0 mg luprolide acetate (Lupron, Tapp Abbott Pharmaceutical Company) was given daily by subcutaneous injection. Within eight weeks, this patient was free of the above described GI symptoms and has remained so to the present time. The patient also no longer required Imuran or prednisone to control her SLE, and her hemoglobin, hematocrit, white blood cells and platelets returned to normal. Compliment levels (C3 and C4) also returned to normal.

Patient number 2 (D. C.) was a 25 year old white woman who presented with severe disabling symptoms of nausea, vomiting and severe abdominal pain. The patient had been previously treated with systemic Imuran and prednisone for control of life threatening symptoms of central nervous system vasculitis. As a result of large and continuous doses of prednisone, she developed bilateral femoral head necrosis and required bilateral femoral head prosthesis.

Treatment with 1.25 mg. of leuprolide acetate (Lupron) was given daily by subcutaneous injection. Within approximately eight weeks of Lupron therapy, this patient was free of gastrointestinal symptoms, and had gained 15–20 pounds.

Patient number 3 (K. B.) was a 32 year old white woman who presented with symptoms of severe nausea, vomiting, and abdominal pain. She was previously diagnosed as having sero-negative SLE, and required Imuran, prednisone, and plaqenil to control this disease. She also required total parental hyperalimentation (TPN) for nutritional control due to her gastrointestinal disorders.

Motility recordings of the stomach and small intestine were performed with a ultraminiature force-transducer probe (Millar Instruments, Houston, Tex.). Pressure readings from the probe were recorded on an R612 physiologic recorder fitted with Model 9872 couplers (SenorMedics, Yorba Linda, Calif.). After the probe was passed transnasally and placed fluoroscopically, a 12 hour recording of the patient was made with the patient in the fasted state. She then drank a 240-ml liquid meal (ENSURE), and the recording was continued for three hours to evaluate conversion from the fasting pattern to fed-state motor activity. During the fasting state, this patient had three poorly formed and disorganized migrating motor complexes, whereas the normal range expected is 6–8, or a mean of 7.4 in the 12 hour recording period. This patient failed to convert to the fed state after drinking the liquid meal. A hydrogen breath test which measures oral-to-cecal transit time was administered, and demonstrated greater than 240 minutes required for transit in this patient, whereas the normal is 90 plus or minus 15 minutes. The patient was diagnosed as having chronic intestinal pseudo-obstruction associated with sero-negative SLE.

Daily administration of 1.75 mg of luprolide acetate (Lupron) was administered subcutaneously. Within eight weeks, her GI symptoms were controlled, and she was able to eat soft, solid food by mouth. This patient has been hospitalized several times since beginning luprolide acetate therapy for exacerbations of her SLE, but the GI tract has not been a factor. Her debilitating symptoms have been controlled, and she was able to return to work.

Patient number 4 (P. W.) was a 38 year old white woman who presented with symptoms of chronic nausea, vomiting and abdominal pain. She was previously diagnosed as having life threatening SLE, and has required Imuran, cytoxan, prednisone and plaqenil to control this disease. Her weight was approximately 78–80 pounds.

She was evaluated as described above with duodenal jejunal manometry and demonstrated virtually no motility during the 12 hour recording session and failed to convert to the fed state after the liquid meal. Her hydrogen breath test was markedly prolonged.

Daily administration of 1.5 mg of luprolide acetate (Lupron) was given by subcutaneous injection. Within eight weeks of Lupron therapy, her GI symptoms were controlled. Although this patient still required intermittent plaqenil and Imuran for control of her SLE, she was able to eat and maintain her nutrition on liquid supplements taken by mouth. Within six months she did not gain weight, but she did not lose weight on oral intake.

After six months of Lupron therapy, motility recordings were again performed. The recording demonstrated six cycling migrating motor complexes, within the normal range. Upon administration of the liquid meal, her motility pattern converted to the fed state indicating functioning nerves of the enteric nervous system and muscle of the small intestine. Patient number 5 (V. H.) was a 70 year old white woman presenting with symptoms of abdominal pain, nausea and vomiting, and a difficult time maintaining weight and nutrition. Evaluation of this patient established diagnosis of SLE, and included positive anti-nuclear antibody of 1:640 and decreased C3 and C4 compliment levels (C3/C4-23/127)

Motility recordings by duodenal jejunal manometry demonstrated an absence of motility of the stomach and small intestine, and failure to convert to the fed state with a liquid meal. Persistent, ongoing, unorganized activity was seen, but was not organized into typical migrating motor complexes. A hydrogen breath test was administered and demonstrated a markedly prolonged oral to cecal transit time.

Daily administration of 1.75 mg luprolide acetate (Lupron) was given subcutaneously. After six months of Lupron therapy, motility recordings were again performed. Ten migrating motor complexes per 12 hour recording session were seen. These complexes were organized and appeared more typical of a controlled tracing, showing normal cycling activity in the stomach and small intestine. She converted to the fed state pattern after intake of the liquid meal. Her hydrogen breath test was unchanged. After six months of therapy, this patient was able to eat foods by mouth and gained weight.

This patient demonstrates that LUPRON therapy was effective in an older, post menopausal patient.

---

I claim:

1. A process for treating a subject exhibiting the symptoms of motility disorders wherein said motility disorder is autonomic neuropathy of Systemic Kupus Erythematosus, comprising:
   administering to the subject a therapeutically effective dosage of a compound comprising an analog of Gonadotropin Releasing Hormone.

2. The process of claim 1, wherein said autoimmune disease is sero-negative Systemic Lupus Erythematosus.

3. A process for treating a subject exhibiting the symptoms of motility disorders associated with autonomic neuropathy of systemic lupus erythematosus, comprising:
   administering to the subject a therapeutically effective dosage of an analog of gonadotropin releasing hormone, wherein said analog is a compound of the formula:

pGlu-His-Trp-Ser-Try-X-Leu-Ary-Pro-NHC$_2$H$_5$, wherein X represents an amino acid of the D-configuration.

4. A process for treating a subject exhibiting the symptoms of motility disorders associated with autonomic neuropathy of systemic lupus erythematosus, comprising:
   administering to the subject a therapeutically effective dosage of a compound comprising an analog of gonadotropin releasing hormone, wherein said analog is a compound of the formula:

pGlu-His-Trp-Ser-Try-D-Leu-Leu-Arg-Pro-HNC$_2$H$_5$.

5. The process of claim 1, wherein said analog is a peptide having an amino acid of the D-configuration at 6-position.

* * * * *

UNITED STATES PATENT AND TRADEMARK OFFICE
CERTIFICATE OF CORRECTION

PATENT NO. : 5,434,136

DATED : Jul. 18, 1995

INVENTOR(S) : John R. Mathias

It is certified that error appears in the above-identified patent and that said Letters Patent is hereby corrected as shown below:

Column 1, line 7, delete "and" after the numeral "616,402" and insert --filed Dec. 14, 1990--.
Column 2, line 57, "HIS" should read --His--.
Column 6, line 43, "(100μm)" should read --(100μl)--.
Column 14, line 36, "develop" should read --developed--; line 48, "luprolide" should read --leuprolide--.
Column 15, lines 34, 38 and 39, "luprolide" should read --leuprolide--;
Column 16, lines 6 and 37, "luprolide" should read --leuprolide--.
Column 17, line 4, "leoprolide" should read --leuprolide--.
Column 23, Claim 1, lines 12 and 13, delete "wherein said motility disorder is" after the word "disorders" and insert therefor --associated with--.
Column 24, Claim 3, line 10, "Ary" should read --Arg--; Claim 4, line 24,"HNC$_2$H$_5$" should read --NHC$_2$H$_5$--.

Signed and Sealed this

Sixth Day of August, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
      ( A ) LENGTH: 10 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:1:

Gly Pro Arg Leu Gly Tyr Ser Trp His Glu (2) INFORMATION FOR SEQ ID NO:2:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..9
        (D) OTHER INFORMATION: /note="GnRH analog"

(xi) SEQUENCE DESCRIPTION: SEQ ID NO:2:

```
Pro  Arg  Leu  Xaa  Tyr  Ser  Trp  His  Glu
 1                   5
```

(2) INFORMATION FOR SEQ ID NO:3:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 4..5
        (D) OTHER INFORMATION: /note="Leucine at position 4 is D-Leucine"

(ix) FEATURE:
        (A) NAME/KEY: Region
        (B) LOCATION: 1..9
        (D) OTHER INFORMATION: /note="leoprolide acetate"

(xi) SEQUENCE DESCRIPTION: SEQ ID NO:3:

```
Pro  Arg  Leu  Leu  Tyr  Ser  Trp  His  Glu
 1                   5
```

(2) INFORMATION FOR SEQ ID NO:4:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 3..4
        (D) OTHER INFORMATION: /note="X at position 3 is Leu, Ile, Val, Met, Phe, nLeu or nVal"

(ix) FEATURE:
        (A) NAME/KEY: Region
        (B) LOCATION: 5..6
        (D) OTHER INFORMATION: /note="X at position 5 is Tyr or Phe"

(xi) SEQUENCE DESCRIPTION: SEQ ID NO:4:

```
Pro  Arg  Xaa  Gly  Xaa  Ser  Trp  His  Glu
 1                   5
```

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: unknown ( i i ) MOLECULE TYPE: peptide ( x i ) SEQUENCE DESCRIPTION: SEQ ID NO:5:

Gly Pro Arg Leu Gly Tyr Ser Trp Glu
1               5

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

Gly Pro Arg Leu Gly Phe Ser Phe His Glu
1               5                   10

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:7:

Gly Pro Arg Leu Gly Tyr Ser Trp Ala Glu
1               5                   10

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 4..5
        ( D ) OTHER INFORMATION: /note="X at position 4 is an amino
            acid of D- configuration"

( x i ) SEQUENCE DESCRIPTION: SEQ ID NO:8:

Pro Arg Leu Xaa Tyr Ser Trp His Glu
1               5

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="X at position 1 is
            Histidine or C(1-3) alkyl"

( i x ) FEATURE:
        ( A ) NAME/KEY: Modified-site
        ( B ) LOCATION: 4..5
        ( D ) OTHER INFORMATION: /note="X at position 4 is Leu, Ile
            or nLeu"

( i x ) FEATURE:

(A) NAME/KEY: Modified-site
(B) LOCATION: 5..6
(D) OTHER INFORMATION: /note="X at position 5 is D-amino acid or synthetic amino acid"

(ix) FEATURE:
(A) NAME/KEY: Modified-site
(B) LOCATION: 6..7
(D) OTHER INFORMATION: /note="X at position 6 is Tyr or Phe"

(xi) SEQUENCE DESCRIPTION: SEQ ID NO:9:

```
Xaa Pro Arg Xaa Xaa Xaa Ser Trp His Glu
1               5                   10
```

(2) INFORMATION FOR SEQ ID NO:10:

(i) SEQUENCE CHARACTERISTICS:
(A) LENGTH: 10 amino acids
(B) TYPE: amino acid
(D) TOPOLOGY: unknown (ii) MOLECULE TYPE: peptide (ix) FEATURE:
(A) NAME/KEY: Modified-site
(B) LOCATION: 5..6
(D) OTHER INFORMATION: /note="X at position 5 is D-Ala"

(ix) FEATURE:
(A) NAME/KEY: Modified-site
(B) LOCATION: 9..10
(D) OTHER INFORMATION: /note="X at position 9 is His, Gly, Asp, Cys, or D-amino acid"

(xi) SEQUENCE DESCRIPTION: SEQ ID NO:10:

```
Gly Pro Arg Leu Xaa Tyr Ser Trp Xaa Glu
1               5                   10
```

(2) INFORMATION FOR SEQ ID NO:11:

(i) SEQUENCE CHARACTERISTICS:
(A) LENGTH: 10 amino acids
(B) TYPE: amino acid
(D) TOPOLOGY: unknown (ii) MOLECULE TYPE: peptide (ix) FEATURE:
(A) NAME/KEY: Modified-site
(B) LOCATION: 5..6
(D) OTHER INFORMATION: /note="X at position 5 is Gly, D-amino acid, or synthetic amino acid"

(xi) SEQUENCE DESCRIPTION: SEQ ID NO:11:

```
Gly Pro Arg Leu Xaa Tyr Ser Trp His Glu
1               5                   10
```

(2) INFORMATION FOR SEQ ID NO:12:

(i) SEQUENCE CHARACTERISTICS:
(A) LENGTH: 10 amino acids
(B) TYPE: amino acid
(D) TOPOLOGY: unknown (ii) MOLECULE TYPE: peptide (ix) FEATURE:
(A) NAME/KEY: Modified-site
(B) LOCATION: 1..2
(D) OTHER INFORMATION: /note="X at position 1 is Az-Gly, Gly having OH replaced by N"

(ix) FEATURE:
(A) NAME/KEY: Modified-site
(B) LOCATION: 5..6

(D) OTHER INFORMATION: /note="X at position 5 is a D-amino acid"

(xi) SEQUENCE DESCRIPTION: SEQ ID NO:12:

Xaa Pro Arg Leu Xaa Tyr Ser Trp His Glu
1           5                   10